United States Patent [19]

Witkowski et al.

[11] Patent Number: 4,847,980
[45] Date of Patent: Jul. 18, 1989

[54] METHOD OF MANUFACTURING TRANSMURAL CARDIAC ELECTRODES

[75] Inventors: Francis X. Witkowski; Patricia A. Penkoske, both of Edmonton, Canada

[73] Assignee: The Governors of the University of Alberta, Edmonton, Canada

[21] Appl. No.: 164,202

[22] Filed: Mar. 4, 1988

[30] Foreign Application Priority Data

Nov. 16, 1987 [CA] Canada .................................. 551949

[51] Int. Cl.⁴ .............................................. H01S 4/00
[52] U.S. Cl. .................................. 29/592.1; 29/825; 29/857; 264/104; 429/219
[58] Field of Search ............... 29/857, 858, 825, 592.1; 264/104, 61; 429/219

[56] References Cited

U.S. PATENT DOCUMENTS

| | | | |
|---|---|---|---|
| 2,654,795 | 10/1953 | Brill et al. ............................. | 429/219 |
| 3,006,821 | 10/1961 | Haring ................................. | 429/219 X |
| 3,332,801 | 7/1967 | Holechek et al. .................... | 264/104 X |
| 3,597,829 | 8/1971 | Wagner et al. ...................... | 29/857 |
| 3,630,779 | 12/1971 | Eisenberg ............................ | 264/104 |
| 3,854,999 | 12/1974 | Thornton ............................. | 264/104 |
| 4,048,404 | 9/1977 | Bro ..................................... | 429/219 X |
| 4,178,339 | 12/1979 | Powell et al. ....................... | 264/104 X |
| 4,324,680 | 4/1982 | Kubota et al. ...................... | 264/61 X |
| 4,368,167 | 1/1983 | Berchielli ............................ | 264/104 |
| 4,519,973 | 5/1985 | Cahalan et al. ..................... | 29/825 X |

FOREIGN PATENT DOCUMENTS

| | | | |
|---|---|---|---|
| 1314538 | 12/1963 | France ................................ | 29/825 |
| 47-40360 | 10/1972 | Japan .................................. | 429/219 |
| 49-9339 | 3/1974 | Japan .................................. | 429/219 |

*Primary Examiner*—Timothy V. Eley
*Assistant Examiner*—Carl J. Arbes
*Attorney, Agent, or Firm*—Sim & McBurney

[57] ABSTRACT

A transmural cardiac electrode includes a base member and at least one hollow needle projecting from it. Each needle has at least one opening in the wall communicating with the hollow center of the needle, and a sintered Ag/AgCl electrode element is positioned within each opening, shielded from electrical contact with the needle, and cemented in position with a nonconducting material. Initially, the electrode element extends beyond the periphery of the needle, but after it is cemented in position it is ground down to conform with the external surface of the needle. An insulated wire is in electrical communication with each electrode element and extends from the opening along the inside of the needle toward and through the base member.

13 Claims, 3 Drawing Sheets

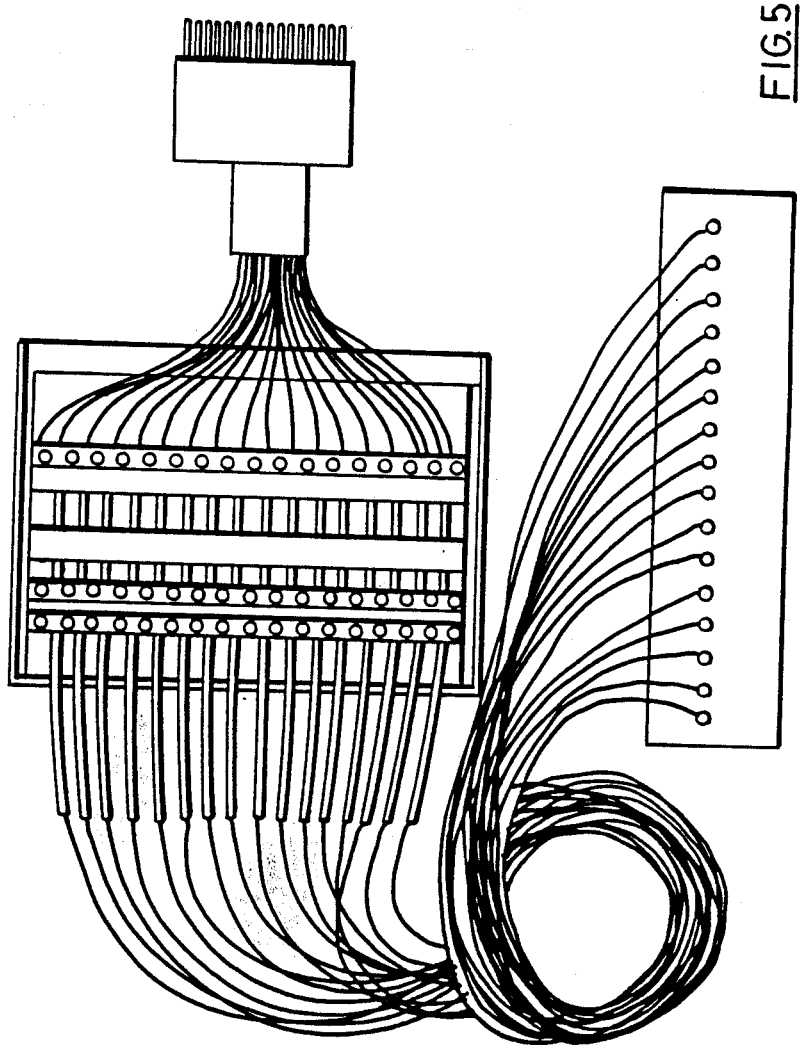

METHOD OF MANUFACTURING TRANSMURAL CARDIAC ELECTRODES

This invention relates generally to a transmural cardiac electrode structure, and a method for manufacturing the electrode.

BACKGROUND OF THIS INVENTION

Many current attempts at electrophysiological elucidation of cardiac arrhythmia mechanisms have centered around activation sequence mapping. This is most commonly performed with polarized unipolar or bipolar metal electrodes, which because of unstable DC baseline potentials, necessitate AC coupled amplification. However, an ideal non-polarizable unipolar electrode would offer unhindered exchange of charge, allowing for stable DC recordings of biological electrical activity. In addition to activation information, DC unipolar recordings enable quantitation of systolic and diastolic potentials, other low frequency phenomena of interest such as repolarization, as well as rapid recovery from such rapid extreme potential shifts such as defibrillation. Previous attempts to apply non-polarizable electrodes to transmural cardiac investigations required complex wick electrode techniques to prevent mechanical movement of the fluid-metal interface when chlorided silver wire was used. We have developed a technique to fabricate miniature sintered Ag/AgCl electrodes that are mounted at various locations on a 20 gauge stainless steel needle permitting stable transmural DC unipolar electrogram recordings in vivo. The electrodes are low noise, rugged, sterilizable and reusable and should prove useful in three-dimensional electrophysiological characterization of the heart.

An electrode is non-polarizable if, when connected to a biological voltage source, a readily reversible chemical reaction occurs within the electrode and there is unhindered ionic exchange. These conditions are best met by using a metal in a solution of its own salt. For biological work Zn/ZnCl2, Hg/HgCl and Ag/AgCl have proven best. Electrodes made of any pure metal all polarize easily and form high-pass filters, eliminating the possibility of directly coupled (DC) recordings. Since the beginning of the twentieth century the Ag/AgCl electrode has shown itself to be the most stable of the easily constructed electrodes.

The larger the surface area, in general, the more stable are the recordings obtained from an electrode. Ag/AgCl electrodes may be fabricated in four ways: (1) electroplating chloride ions onto a pure Ag base; (2) coating a pure Ag base with molten AgCl; (3) suspending powdered Ag and AgCl in an electrically conductive matrix (1); (4) compressing a fine powder of Ag and AgCl and then heating to slightly below the melting point of the AgCl (melting point of AgCl=455° C., melting point of Ag=960.8° C.) to fuse the particles only at their points of contact. This fourth process is called sintering. It has the singular advantage of maintaining a large effective surface area in a small physical size. It also ensures some degree of mechanical strength, and in the case of metals, electrical continuity throughout the sintered object.

Techniques for making large sintered Ag/AgCl electrodes for cardiac recordings are known. DC potentials obtained with non-polarizable electrodes have permitted elucidation of the mechanisms of the ST segment elevation on the ECG seen commonly with acute myocardial ischemia and mapping of the associated injury currents. These results have been corroborated with DC magnetic field recordings which do not rely on an electrode interface to translate the biologically generated signal carried by ions to one carried electronically by electrons.

Neither the electrophysiological alterations induced by myocardial ischemia nor the pattern of normal activation and repolarization are homogeneous throughout the thickness of the ventricles in either man or in canine models. These require transmural recording techniques. Previous investigators have developed elegant wick electrode recording techniques to physically remove the electrode from the beating heart to obtain stable DC baselines within ±1 mV over the duration of an experiment (1–2 hours) To apply such techniques to obtain transmural recordings from hundreds of sites in vivo simultaneously would present major methodological difficulties. To address this problem we have developed an easily implanted non-polarizable needle electrode containing multiple transmural recording sites based on sintered Ag/AgCl technology.

GENERAL DESCRIPTION OF THIS INVENTION

Accordingly, this invention provides a transmural cardiac electrode, comprising:
a base member,
at least one hollow needle projecting from and supported by said base member,
at least one opening in the wall of each needle communicating with the hollow centre of the needle,
a sintered Ag/AgCl electrode element positioned within each opening and shielded from electrical contact with the needle, the electrode element being cemented in position with a non-conducting material, the electrode element being ground to conform with the external surface of the hollow needle,
and an insulated wire in electrical communication with each electrode element and extending from said opening, along the inside of the needle, toward and through the base member.

Further, this invention provides a method for manufacturing a transmural cardiac electrode, comprising the steps:

(a) compressing a fine Ag/AgCl powder around the bared end of an insulated wire to form therefrom an electrode element, (b) sintering the electrode element in a sintering furnace at a temperature slightly below the melting temperature of AgCl, (c) providing a base member from which projects a hollow needle with an opening in the wall of the needle in communication with the hollow centre of the needle, (d) threading the loose end of the wire through the hollow needle from the opening, (e) using non electrically conductive material to cement the electrode element in place within the opening in such a way that (1) the electrode element is shielded from electrical contact with the needle, and (2) the electrode element projects outwardly beyond the outer periphery of the needle, and (f) grinding the outwardly projecting portion of the electrode element down to conform to the periphery of the needle.

Finally, this invention provides a method for manufacturing a transmural cardiac electrode, comprising the steps:

(a) compressing a plurality of batches of fine Ag-/AgCl powder around the bared ends of a plurality of insulated wires to form therefrom a plurality of electrode elements, (b) sintering the electrode elements in a sintering furnace at a temperature slightly below the melting temperature of AgCl, (c) providing a base member from which projects a plurality of hollow needles each having at least one opening in the wall of the needle in communication with the hollow centre of the needle, (d) threading the loose end of each wire through the respective hollow needle from the opening, (e) using non electrically conductive material to cement each electrode element in place within the respective opening in such a way that (1) the electrode element is shielded from electrical contact with the needle, and (2) the electrode element projects outwardly beyond the outer periphery of the needle, and (f) grinding the outwardly projecting portion of each electrode element down to conform to the periphery of the respective needle.

GENERAL DESCRIPTION OF THE DRAWINGS

One embodiment of this invention is illustrated in the accompanying drawings, in which like numerals denote like parts throughout the several views, and in which:

FIG. 1 is a sectional view through a compression die, used in the method of this invention;

FIGS. 2A, 2B ad 2C illustrate three sequential steps in the manufacture of the electrode of this invention;

FIG. 5 is a view of a multi-needle electrode array, constructed in accordance with this invention.

DETAILED DESCRIPTION OF THE DRAWINGS

The steps carried out in the manufacture of the electrode in accordance with this invention will first be described, as this will clarify the construction.

Figure 1:
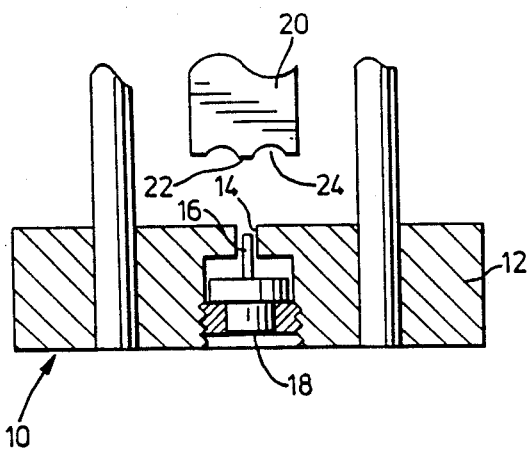

A Teflon insulated 130 μm (0.005 inch) Ag wire is cut to a 5 cm length, and is stripped bare at one end for 1-2 mm using a thermal wire stripper such as HOTWEEZ-ERS Model No. 4A (Meisei Corporation, Los Angeles, Calif.). The bare portion of the wire is formed into a small single loop with an outside diameter of approximately 0.5 mm. Finely powdered 50:50 Ag/AgCl is then compressed over this bare wire loop in a steel die seen at 10 in FIG. 1, using an arbor press. The press incorporates a fixed base 12 having a cylindrical die opening 14, in which is located a cylindrical anvil 16 of which the vertical position is adjustable by means of an externally threaded nut 18. Thus, the depth of the die cavity is adjustable. The die 20 incorporates a downwardly projecting circular portion 22, surrounded by an annular cavity 24 to allow excess powder to escape.

In the compression operation, care must be taken not to damage either the thin Teflon insulation on the wire protruding from the electrode, or the Ag wire loop within the electrode. A compression pressure of between 5,000 and 10,000 psi has been found to be satisfactory.

The result of the compression is to form the powder into a right circular cylinder encompassing the looped and bared end of the wire. This cylinder is then suspended by the end of the attached wire in a sintering furnace, for example Model 51442 furnace with 59344 temperature controller, Lindberg, watertown, WIS, at about 10° C. below the melting point of AgCl (m.p.=455° C.) for about 1.5 hours. Care must be taken to prevent contamination of the Ag/AgCl electrode or its Teflon insulated wire with other objects while in the furnace, since the Teflon becomes sticky, but does not melt, at this high temperature. The high temperature will change the Teflon insulation from transparent to white.

Once baked, the sintered Ag/AgCl electrode element is ready to be mounted.

Figure 2A:
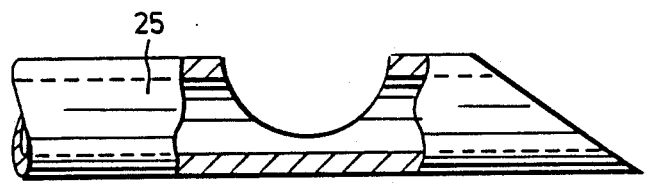
Figure 2B:
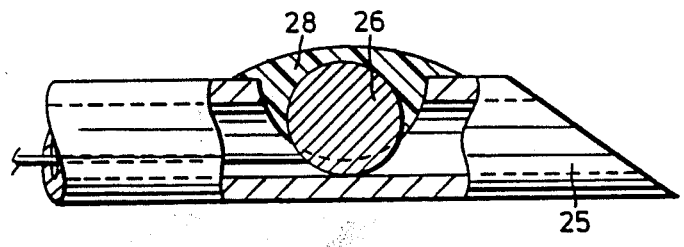

The next step is to grind a short bevel 20 gauge stainless steel needle as shown in FIG. 2A at two axially separated locations to provide access to the needle interior. The needles are then cut to the desired length. For canine experiments, we have used a 4 mm interelectrode distance for free ventricular wall needle electrodes and a 10 mm interelectrode distance for septal needle electrodes. To deburr the future electrode sites after needle grinding, a motorized hand tool is mounted vertically in the part of a microscope stand that normally houses the objectives. The needle is mounted where the slide would normally go and this, together with a dissecting microscope for visualization, forms an inexpensive but accurate micro-milling machine. Once the needle sites are deburred, the surfaces are degreased and dried. The Ag/AgCl electrode element with its electrically and mechanically bonded Teflon insulated Ag wire is then slid into the needle cavity after first feeding the wire up from the opening through the hollow centre of the needle. The electrode element should be cushioned on a bed of insulating epoxy and care must be taken not to allow electrical contact between the electrode element and the needle. The preferred orientation of the electrode element (in the form of a right circular cylinder) is one in which its axis extends laterally across the opening and perpendicular to the axis of the needle. This is clearly seen in FIGS. 2B and 2C. In order to monitor for electrical shorts between the electrode and the needle, an audible continuity tester can be connected between the Ag wire protruding from the blunt end of the needle and the needle body. To ensure the three-dimensional position of the Ag/AgCl electrode while the epoxy sets, we again employed a microscope stand as previously described but with a small piece of Teflon tubing rigidly mounted to the top arm of the microscope that slips onto the Ag/AgCl electrode with the needle mounted to the movable stage. Teflon is used since it will not stick to the cured epoxy The stage of the microscope stand is then locked in the desired location, and the entire microscope stand, with its captive needle mounted electrode, is placed in an oven at 60° C. to rapidly cure the epoxy. This takes about 1 hour. We have found that the quick setting epoxies, by contrast, failed to have the desired adhesive, machinability and durability qualities that were needed.

Figure 2C:
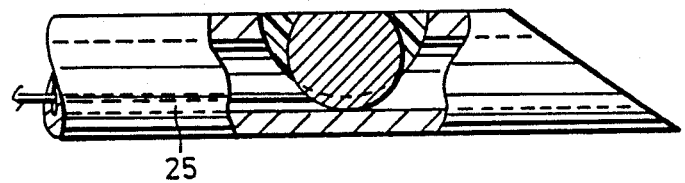

Once the setting has taken place, the second Ag/AgCl electrode is similarly mounted in the needle. Epoxy is then spread over both electrodes to fill any remaining gaps, and is allowed to cure. Then, the excess is polished off as seen in FIG. 2C. This is done by microgrinding and results in an electrode face which has an substantial extent, and certainly much greater than the diameter of the silver wire to which it is connected.

The needle is then connected to an epicardial shoulder 30 (see FIG. 4) which is fabricated from a filled phenolic rod of 4.8 mm diameter, cut into 0.8 mm slices with one hole in its center for the needle and one hole between the center and outside edge into which a third Ag/AgCl cylinder 32 is pressed. Phenolic is used for its rigidity and its durable bonding to epoxy. The needle 25, with its two Ag/AgCl electrodes 26 mounted along its length, is inserted into this phenolic disc 34, and epoxied at the correct distance from the phenolic disc to the first intramural recording site.

Figure 3:
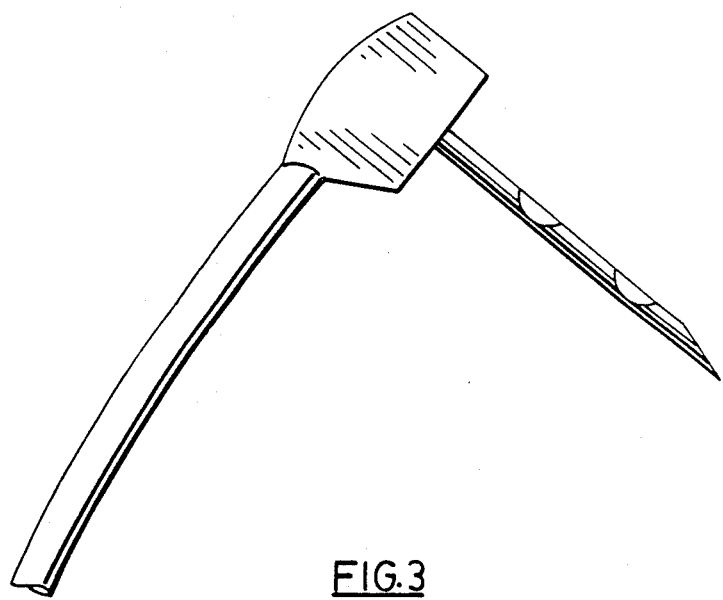
FIG. 3 is an elevational view of a single-needle version of this invention.
Figure 4:
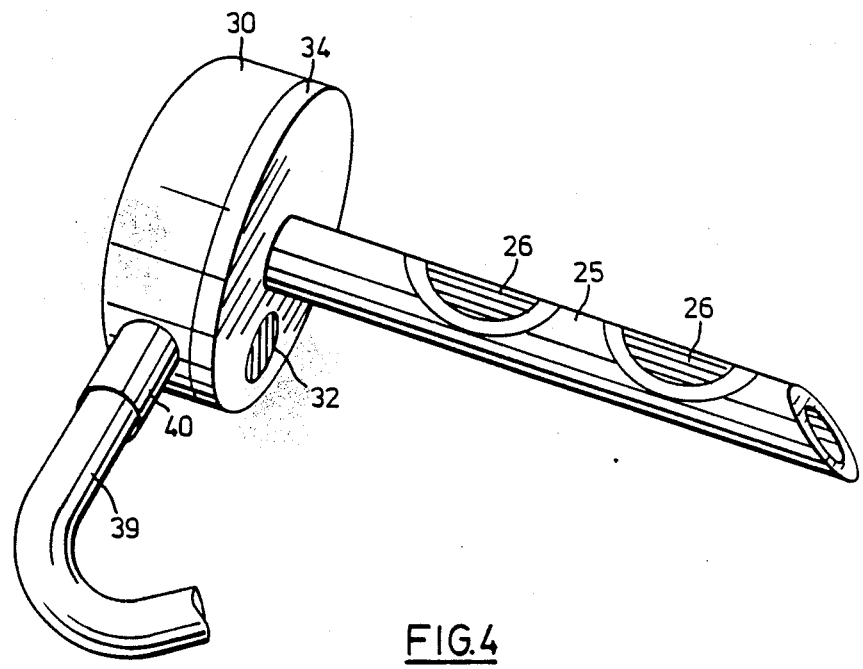
FIG. 4 is a perspective view, with certain dimensions exaggerated for the sake of clarity, of a single-needle electrode constructed in accordance with this invention.

The three insulated Ag wires are then connected to a flexible shielded cable 39, and the shield of the cable is connected to the guard circuit of the first amplification stage. We have used a polyvinylchloride jacketed subminiature cable (NMUF 3/38-1650SJ, Cooner Wire Company, Chatsworth, Calif.), which is flexible with a plated copper shield, but will not firmly bind to epoxy. To overcome this, a 5 mm length of stainless steel hypodermic tubing 40 is crimped onto the end of the cable jacket The needle with its mounted phenolic collar is then inserted into a mold machined from Teflon and the cable with its crimped strain relief is mounted at right angles to the needle in the mold. The positioning of the wire at right angles is necessary for in vivo applications on the posterior aspect of the heart. The interconnections are soldered and the mold is filled with epoxy to cover all exposed wiring to eliminate dissimilar metal junction potentials and to ensure structural durability. The completed needle electrode is illustrated in FIG. 4 with a somewhat exaggerated needle diameter, and more accurately in FIG. 3.

An array of 16 such needle electrodes is shown in FIG. 5. The epoxy back of each electrode can be colour coded and numbered for easy identification. This electrode array provides 48 unipolar transmural recording sites from 16 epicardial insertion sites with a single electrical interconnection.

Electrode Conditioning Prior to Use

Since all electrodes are miniature batteries, the inherent DC potential between any two electrodes is a factor of major importance. The reference electrode for our unipolar electrogram recordings is a 4 mm sintered Ag/AgCl disc electrode mounted with epoxy to a small sewing patch of Teflon, which is then sutured to the root of the aorta. Prior to use however, each electrode and the reference must be brought into equilibrium. This may be accomplished by storing the electrodes for 2-4 hours prior to use in a 0.9% saline solution with the leads shorted together to form a complete circuit. Using this technique, in vivo and in vitro DC stabilities of $\pm 1$ mV can be readily achieved.

We have found that the non-polarizable unipolar electrodes constructed in accordance with this invention permit stable DC recordings of biological electrical activity and permit excellent quantitation of systolic and diastolic potentials, other low frequency phenomena of interest such as repolarization, as well as rapid recovery from such rapid extreme potential shifts as defibrillation.

While one embodiment of this invention has been illustrated in the accompanying drawings and described hereinabove, it will evident to those skilled in the art that changes and modifications may be made therein without departing from the essence of this invention, as set forth in the appended claims The embodiments of the invention in which an exclusive property or privilege is claimed are defined as follows:

1. A method for manufacturing a transmural cardiac electrode, comprising the steps
   (a) compressing a fine Ag/AgCl powder around the bared end of an insulated wire to form therefrom an electrode element,
   (b) sintering the electrode element in a sintering furnace at a temperature slightly below the melting temperature of AgCl,
   (c) providing a base member from which projects a hollow needle with an opening in the wall of the needle in communication with the hollow centre of the needle,
   (d) threading the loose end of the wire through the hollow needle from the opening,
   (e) using non electrically conductive material to cement the electrode element in place within the opening in such a way that (1) the electrode element is shielded from electrical contact with the needle, and (2) the electrode element projects outwardly beyond the outer periphery of the needle, and
   (f) grinding the outwardly projecting portion of the electrode element down to conform to the periphery of the needle.

2. The invention claimed in claim 1 in which the electrode element is substantially in the form of a right circular cylinder, and is cemented in place within the opening with its axis extending laterally across the opening.

3. The invention claimed in claim 1, in which the temperature of the sintering furnace is about 445 degrees Celsius, and the duration of the sintering step is about 1.5 hours.

4. The invention claimed in claim 1, in which the non electrically conductive material cementing the electrode element in place is an epoxy.

5. The invention claimed in claim 1, in which the wire is a Teflon insulated silver wire of about 0.005 inch diameter.

6. The invention claimed in claim 1, in which step (a) is carried out by compressing the fine powder in a steel die using a pressure between about 5,000 and about 10,000 psi.

7. The invention claimed in claim 2, in which the temperature of the sintering furnace is about 445 degrees Celsius, and the duration of the sintering step is about 1.5 hours.

8. The invention claimed in claim 7, in which the non electrically conductive material cementing the electrode element in place is an epoxy.

9. The invention claimed in claim 8, in which the wire is a Teflon insulated silver wire of about 0.005 inch diameter.

10. The invention claimed in claim 9, in which step (a) is carried out by compressing the fine powder in a steel die using a pressure between about 5,000 and about 10,000 psi 11. A method for manufacturing a transmural cardiac electrode, comprising the steps:
    (a) compressing a plurality of batches of fine Ag/AgCl powder around the bared ends of a plurality of insulated wires to form therefrom a plurality of electrode elements, (b) sintering the electrode elements in a sintering furnace at a temperature slightly below the temperature of AgCl,
(c) providing a base member from which projects a plurality of hollow needles each having at least one opening in the wall of the needle in communication with the hollow centre of the needle,
(d) threading the loose end of each wire through the respective hollow needle from the opening,
(e) using non electrically conductive material to cement each electrode element in place within the respective opening in such a way that (1) the electrode element is shielded from electrical contact with the needle, and (2) the electrode element projects outwardly beyond the outer periphery of the needle, and (f) grinding the outwardly projecting portion of each electrode element down to conform to the periphery of the respective needle.

12. The invention claimed in claim 11, in which there are two openings in each needle.

13. The invention claimed in claim 11, in which each electrode element is substantially in the form of a right circular cylinder, and is cemented in place within its opening, using epoxy, with the axis of the cylinder extending laterally across the opening and perpendicular to the needle axis, in which the temperature of the sintering step is about 445 degrees Celsius and the duration of the sintering step is about 1.5 hours, and in which step (a) is carried out by compressing the fine powder in a steel die using a pressure between about 5,000 and about 10,000 psi.

* * * * *